(12) United States Patent
Koyakumaru et al.

(10) Patent No.: US 6,197,962 B1
(45) Date of Patent: Mar. 6, 2001

(54) METHOD FOR PRODUCING 2-SULFONYLPYRIDINE DERIVATIVES AND METHOD FOR PRODUCING 2-{[(2-PYRIDYL)METHYL]THIO}-1H-BENZIMIDAZOLE DERIVATIVES

(75) Inventors: Ken-ichi Koyakumaru; Takashi Sugioka; Tomoya Kuwayama; Goro Asanuma, all of Okayama (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 09/236,444

(22) Filed: Jan. 25, 1999

(30) Foreign Application Priority Data

| Jan. 26, 1998 | (JP) | ................................. 10-012554 |
| Nov. 13, 1998 | (JP) | ................................. 10-323653 |
| Nov. 13, 1998 | (JP) | ................................. 10-323654 |

(51) Int. Cl.$^7$ .................................................. C07D 401/12
(52) U.S. Cl. ........................ 546/273.7; 546/295; 546/296; 546/297; 546/298
(58) Field of Search ..................... 546/295, 296, 546/297, 298, 273.7

(56) References Cited

U.S. PATENT DOCUMENTS

| 4,255,431 | 3/1981 | Junggren et al. | .................. 546/273.7 |
| 4,544,750 | 10/1985 | Braendstroem et al. | ......... 546/273.7 |
| 4,897,488 | 1/1990 | Gallenkamp et al. | ............... 546/345 |

FOREIGN PATENT DOCUMENTS

| 642 359 | 4/1984 | (CH) . |
| 0 484 265 | 5/1992 | (EP) . |
| 0 882 713 | 12/1998 | (EP) . |
| 0 899 268 | 3/1999 | (EP) . |
| 5-70434 | 3/1993 | (JP) . |
| 9-59254 | 3/1997 | (JP) . |
| WO 96/26188 | 8/1996 | (WO) . |
| WO 97/29103 | 8/1997 | (WO) . |
| WO 98/11071 | 3/1998 | (WO) . |

OTHER PUBLICATIONS

U. Rueffer, et al., Synthesis, pp. 623–625, "5–Alkyl–2–(p–Tolylsulfonyl)Pyridines By Regioselective Cyano [4+2] Cycloaddition", Aug., 1989.

N. Furukawa, et al., J. Chem. Soc. Perkin. Trans. I, pps. 1839–1845, "ipso–Substitution Of A Sulphinyl Or Sulphonyl Group Attached To Pyridine Rings And Its Application For The Synthesis Of Macrocycles", 1984.

M.S.A. Vruland, Organic Synthesis, vol. 6, pp. 727–730, "Sulfonyl Cyanides: Methanessulfonyl Cyanide", 1988.

CA 125:275662, Terashima et al., 1996.*
CA 120:107017, Palomo, 1996.*

* cited by examiner

*Primary Examiner*—Jane Fan
(74) *Attorney, Agent, or Firm*—Oblon, Spivak, McClelland, Maier & Neustadt, P.C.

(57) ABSTRACT

2-Sulfonylpyridine derivatives can be industrially produced efficiently by reacting a sulfonyl cyanide derivative with an α, β-unsaturated carbonyl compound and a 2-{[(2-pyridyl)methyl]thio}-1H-benzimidazole skeleton can be formed in one step in a good yield by reacting this type of the 2-sulfonylpyridine derivative with a 2-methylthio-1H-benzimidazole derivative in the presence of an organolithium compound.

2 Claims, No Drawings

METHOD FOR PRODUCING 2-SULFONYLPYRIDINE DERIVATIVES AND METHOD FOR PRODUCING 2-{[(2-PYRIDYL)METHYL]THIO}-1H-BENZIMIDAZOLE DERIVATIVES

BACKGROUND OF THE INVENTION

1. Field of the Invention

The present invention relates to a method for producing 2-sulfonylpyridine derivatives. The 2-sulfonylpyridine derivatives produced by the present invention are useful as starting materials for synthesis of drugs, agricultural chemicals, etc., such as the synthesis starting materials of drug intermediates, including 5-aminomethyl-2-chloropyridine which is useful as an intermediate for synthesis of chloronicotinyl pesticides, 2,5-dichloropyridine which is an intermediate for synthesis of lazabemide, whose clinical development as an anti-Parkinson's disease drug is being promoted, 2-hydroxypyridine, etc. (refer to U.S. Pat. No. 4,897,488, International Patent Application Laid-open No. WO96/26188, International Patent Application Laid-open No. WO98/11071, and Japanese Patent Application Laid-open No. 9-59254).

Moreover, the present invention relates to a method for producing 2-{[(2-pyridyl)methyl]thio}-1H-benzimidazole derivatives. The 2-{[(2-pyridyl)methyl]thio}-1H-benzimidazole derivatives obtained by the present invention are useful as, for instance, intermediates of 2-{[(2-pyridyl)methyl]sulfinyl}-1H-benzimidazole derivatives, compounds related to omeprazole, which is useful as an anti-ulcer agent.

2. Related Art of the Invention

Many physiologically active substances with a pyridine skeleton have been discovered in recent years. As methods for producing 2-sulfonylpyridine derivatives that are useful as intermediates for synthesis of these compounds, there are known, for example:

(1) The method in which sulfonyl cyanide is reacted with an acyloxybutadiene derivative (refer to International Patent Application Laid-open No. WO96/26188);

(2) The method in which p-toluenesulfonyl cyanide is reacted with 1-ethoxy-2-methylbutadiene (refer to *Synthesis*, p. 623 (1989) and International Patent Application Laid-Open No. WO98/11071);

(3) The synthesis method in which 2-halogenopyridine is reacted with an alkali metal thiolate to produce sulfenylpyridine, and then the sulfenylpyridine is gradually oxidized (refer to *Journal of the Chemical Society Perkin Transaction* 1, page 1839 (1984)).

However, the above-mentioned methods (1) and (2) have problems in that they have to use a diene compound that is thermally unstable, and the above-mentioned method (3) has problems in that there are many steps, the desired product yield is low, etc., and therefore, these methods can not be considered to be industrially efficient methods for producing 2-sulfonylpyridine derivatives.

In addition, the method in which a 2-halomethylpyridine derivative is reacted with a metal salt of a 2-mercapto-1H-benzimidazole derivative is known as a method for producing a 2-{[(2-pyridyl)methyl]thio}-1H-benzimidazole derivative, and when this is oxidized, a 2-{[(2-pyridyl)methyl]sulfinyl}-1H-benzimidazole derivative can be obtained (refer to U.S. Pat. No. 4,255,431). The 2-halomethylpyridine derivative that is used as the starting material for this method is produced via many steps using 2,3,5-trimethylpyridine as the starting material (refer to, for instance, U.S. Pat. No. 4,544,750 and Japanese Patent Application Laid-open No. 5-70434).

However, conventional methods for producing 2-{[(2-pyridyl)methyl]thio}-1H-benzimidazole derivatives can not be considered to be efficient production methods because many steps are needed to produce the starting 2-halomethylpyridine derivative. Moreover, there are problems in that 2-halomethylpyridine derivatives have poor shelf life and they must therefore be used in the next reaction immediately after synthesis.

SUMMARY OF THE INVENTION

The object of the present invention is to provide a method for producing 2-sulfonylpyridine derivatives industrially with efficiency in a good yield under moderate conditions.

Moreover, another object of the present invention is to provide a novel method for producing, efficiently synthesized in a short process, 2-{[(2-pyridyl)methyl]thio}-1H-benzimidazole derivatives, which are precursors of 2-{[(2-pyridyl)methyl]sulfinyl}-1H-benzimidazole derivatives.

The inventors have found that a 2-sulfonylpyridine derivative can be industrially produced efficiently by reacting a sulfonyl cyanide derivative with an α, β-unsaturated carbonyl compound and that a 2-{[(2-pyridyl)methyl]thio}-1H-benzimidazole skeleton can be formed in one step in a good yield by reacting this type of 2-sulfonylpyridine derivative with a 2-methylthio-1H-benzimidazole derivative in the presence of an organolithium compound, and completed the present invention based on these findings.

That is, the present invention provides a method for producing a 2-sulfonylpyridine derivative represented by the formula (III)

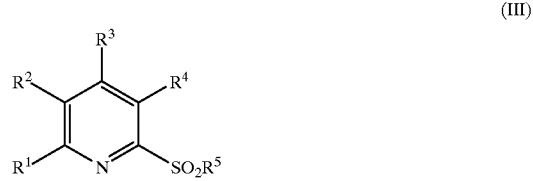

(III)

(In the formula, $R^1$ is a hydrogen atom or an alkyl group or an aryl group that may be substituted, $R^2$ and $R^3$ are a hydrogen atom, a halogen atom, or an alkyl group or an aryl group that may be substituted, $R^4$ is a hydrogen atom, a halogen atom, an alkoxyl group, an alkylthio group, a cyano group, an acyloxy group, an alkoxycarbonyl group, a protected amino group that may be substituted, or an alkyl group or an aryl group that may be substituted, and together $R^2$ and $R^3$ or $R^3$ and $R^4$ can represent —$(CH_2)_n$—(n is 3 or 4.), and $R^5$ is an alkyl group, a cycloalkyl group, an aryl group or an aralkyl group that may be substituted.), which method comprises:

reacting an α, β-unsaturated carbonyl compound represented by general formula (I)

(I)

(In the formula, $R^1$, $R^2$, $R^3$ and $R^4$ are the same as previously defined.)

with a sulfonyl cyanide represented by general formula (II)

(II)

(In the formula, $R^5$ is the same as previously defined.)
to obtain the 2-sulfonylpyridine derivative represented by general formula (III).

Moreover, the present invention provides a method for producing a 2-{[(4-alkoxy-2-pyridyl)methyl]thio}-1H-benzimidazole derivatives (VII)

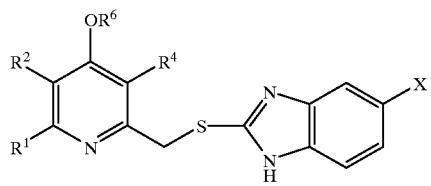
(VII)

(In the formula, $R^1$, $R^2$ and $R^4$ are the same as previously defined. X is a hydrogen atom, a halogen atom or an alkyl group, an alkenyl group, an aryl group, an aralkyl group or an alkoxyl group that may be substituted, and $R^6$ is an alkyl group.), which method comprises:

reacting a halogeno-α, β-unsaturated carbonyl compound represented by general formula (I-1)

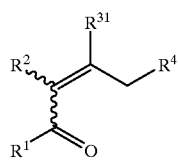
(I-1)

(In the formula, $R^1$, $R^2$ and $R^4$ are the same as previously defined, and $R^{31}$ is a halogen atom.)
with a sulfonyl cyanide represented by general formula (II)

(II)

(In the formula, $R^5$ is the same as previously defined.)
to obtain a 4-halogeno-2-sulfonylpyridine derivative represented by general formula (III-1)

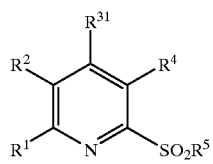
(III-1)

(In the formula, $R^1$, $R^2$, $R^{31}$, $R^4$ and $R^5$ are the same as previously defined.), reacting the obtained derivative of general formula (III-1) in the presence of an organolithium compound with a 2-methylthio-1H-benzimidazole derivative represented by general formula (IV)

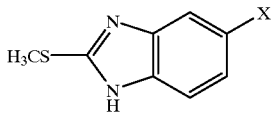
(IV)

(In the formula, X is the same as previously defined.)
to obtain a 2-{[(4-halogeno-2-pyridyl)methyl]thio}-1H-benzimidazole derivative represented by general formula (V)

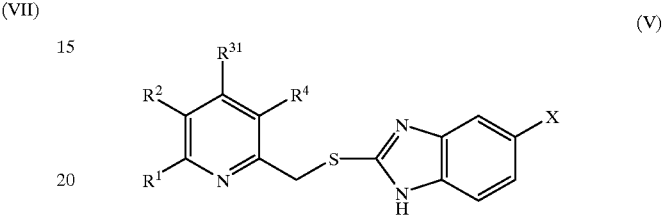
(V)

(In the formula, $R^1$, $R^2$, $R^{31}$, $R^4$ and X are the same as previously defined.),
reacting the obtained derivative of general formula (V) with a metal alkoxide represented by general formula (VI)

(VI)

(In the formula, $R^6$ is the same as defined above, and M is an alkali metal or an alkaline earth metal.),
to obtain the 2-{[(4-alkoxy-2-pyridyl)methyl]thio}-1H-benzimidazole derivative represented by general formula (VII).

In addition, the present invention provides a method for producing a 2-{[(4-halogeno-2-pyridyl)methyl]thio}-1H-benzimidazole derivative represented by general formula (V)

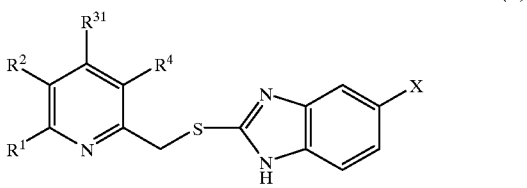
(V)

(In the formula, $R^1$, $R^2$, $R^{31}$, $R^4$ and X are the same as previously defined.), which method comprises:

reacting, in the presence of an organolithium compound, a 4-halogeno-2-sulfonylpyridine derivative represented by general formula (III-1)

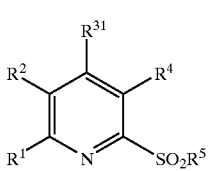
(III-1)

(In the formula, $R^1$, $R^2$, $R^{31}$, $R^4$ and $R^5$ are the same as previously defined.),
with a 2-methylthio-1H-benzimidazole derivative represented by general formula (IV)

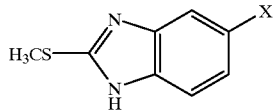

(In the formula, X is the same as previously defined.), to obtain the derivative of general formula (V).

The present invention also provides a 4-chloro-3,5-dimethyl-2-sulfonylpyridine derivative represented by general formula (III-1a)

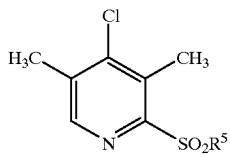

(In the formula, $R^5$ is the same as previously defined.).

The present invention further provides a method for producing a 2-{[(4-alkoxy-2-pyridyl)methyl]thio}-1H-benzimidazole derivative represented by general formula (VII)

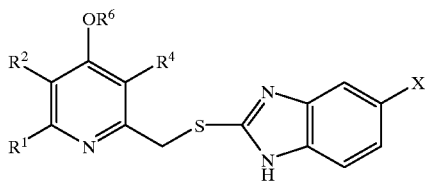

(In the formula, $R^1$, $R^2$, $R^4$, $R^6$ and X are the same as previously defined.), which method comprises:

reacting a 2-{[(4-halogeno-2-pyridyl)methyl]thio}-1H-benzimidazole derivative represented by general formula (V)

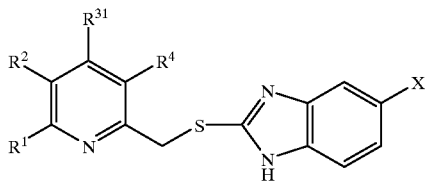

(In the formula, $R^1$, $R^2$, $R^{31}$, $R^4$ and X are the same as previously defined.),
with a metal alkoxide represented by general formula (VI)

$$R^6OM \qquad (VI)$$

(In the formula, $R^6$ and M are the same as previously defined.), to obtain the derivative of general formula (VII).

The present invention also provides a 2-{[(4-chloro-3,5-dimethyl-2-pyridyl)methyl]thio}-1H-benzimidazole derivative represented by general formula (V-1)

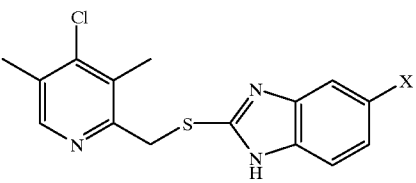

(In the formula, X is the same as previously defined.).

Moreover, the present invention provides a method for producing a 2-{[(4-alkoxy-2-pyridyl)methyl]thio}-1H-benzimidazole derivative represented by general formula (VII)

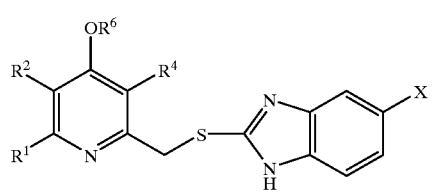

(In the formula, $R^1$, $R^2$, $R^4$, $R^6$ and X are the same as previously defined.), which method comprises:

reacting, in the presence of an organolithium compound, an 4-alkoxy-2-sulfonylpyridine derivative represented by general formula (VIII)

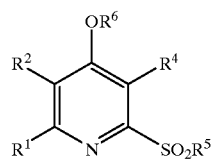

(In the formula, $R^1$, $R^2$, $R^4$, $R^5$ and $R^6$ are the same as previously defined.), with a 2-methylthio-1H-benzimidazole derivative represented by general formula (IV)

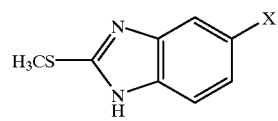

(In the formula, X is the same as previously defined.), to obtain the derivative of general formula (VII).

The present invention also provides a 4-methoxy-3,5-dimethyl-2-sulfonylpyridine derivative represented by general formula (VIII-1)

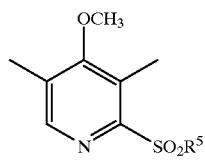
(VIII-1)

(In the formula, $R^5$ is the same as previously defined.).

These and other objects, features and advantages of the present invention are described in or will become apparent from the following detailed description of the invention.

DETAILED DESCRIPTION OF THE INVENTION

The present invention will be described in detail while referring to the following reaction scheme.

Reaction Scheme

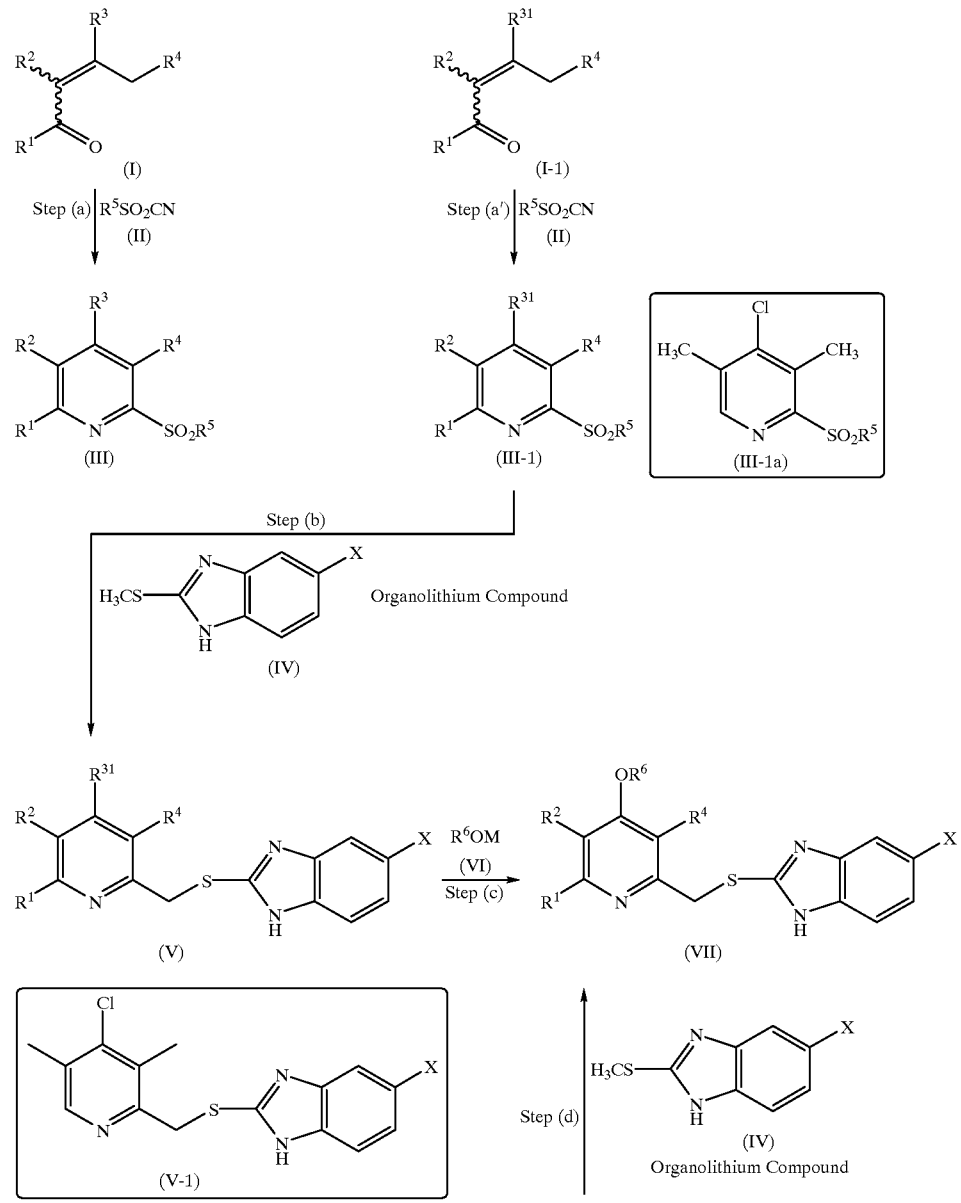

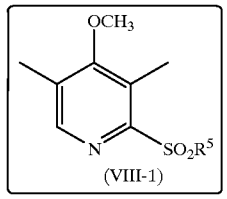 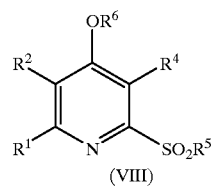

First, the substitution groups in the general formulas shown in the above mentioned reaction scheme will be described.

Examples of the alkyl groups represented by each of $R^1$, $R^2$, $R^3$, $R^4$, $R^5$ and X include linear or branched alkyl groups such as a methyl group, an ethyl group, a propyl group, an isopropyl group, a butyl group, an isobutyl group, a tert-butyl group and a hexyl group. These alkyl groups may be substituted with, e.g., halogen atoms such as a chlorine atom, a bromine atom, an iodine atom and a fluorine atom; alkoxyl groups such as a methoxy group, an ethoxy group, a propoxy group and a butoxy group; a hydroxyl group; tri-substituted silyloxy groups such as a tert-butyldimethylsilyloxy group and a tert-butyl diphenylsilyloxy group; a nitro group.

Examples of the aryl groups represented by each of $R^1$, $R^2$, $R^3$, $R^4$, $R^5$ and X include a phenyl group, a naphthyl group, etc. These aryl groups may be substituted with, e.g., halogen atoms such as a chlorine atom, a bromine atom, an iodine atom and a fluorine atom; alkoxyl groups such as a methoxy group, an ethoxy group, a propoxy group and butoxy group; alkyl groups such as a methyl group, en ethyl group, a propyl group and butyl group; a hydroxyl group; tri-substituted silyloxy groups such as a tert-butyldimethylsilyloxy group and a tert-butyldiphenylsilyloxy group; a nitro group; and aryl groups such as a phenyl group and p-methoxyphenyl group.

Examples of the alkoxyl groups represented by $R^4$ include a methoxy group, an ethoxy group, a propoxy group, a butoxy group and a phenoxy group. Examples of the alkylthio groups represented by $R^4$ include a methylthio group, an ethylthio group, a propylthio group and a butylthio group. Examples of the acyloxy groups represented by $R^4$ include aliphatic or aromatic acyloxy groups such as an acetoxy group, a propanoyloxy group, a butanoyloxy group, a pivaloyloxy group and a benzoyloxy group. Examples of the alkoxycarbonyl groups represented by R4 include a methoxycarbonyl group, en ethoxycarbonyl group and a n-butoxycarbonyl group. Examples of the protected amino groups represented by $R^4$ include amino groups that are protected by protecting groups such as an acetyl group, a benzoyl group, a benzenesulfonyl group, and a tert-butoxycarbonyl group, and that may be substituted with, e.g., alkyl groups such as a methyl group, an ethyl group a propyl group, an isopropyl group, a butyl group, an isobutyl group and tert-butyl group.

Examples of the cycloalkyl groups represented by $R^5$ include a cyclopropyl group, a cyclopentyl group and cyclohexyl group. These cycloalkyl groups may be substituted with, e.g., halogen atoms such as a chlorine atom, a bromine atom, an iodine atom and a fluorine atom; alkoxyl groups such as a methoxy group, an ethoxy group, a propoxy group and butoxy group; a hydroxyl group; tri-substituted silyloxy groups such as a tert-butyldimethylsilyloxy group and a tert-butyldiphenylsilyloxy group; a nitro group; and aryl groups such as a phenyl group and a p-methoxyphenyl group.

Examples of the aralkyl groups represented by $R^5$ and X include a benzyl group and a phenethyl group. These aralkyl groups may be substituted with, e.g., halogen atoms such as a chlorine atom, a bromine atom, an iodine atom and a fluorine atom; alkoxyl groups such as a methoxy group, an ethoxy group, a propoxy group and a butoxy group; alkyl groups such as a methyl group, an ethyl group, a propyl group, an isopropyl group and a butyl group; a hydroxyl group; tri-substituted silyloxy groups such as a tert-butyldimethylsilyloxy group and a tert-butyldiphenylsilyloxy group; a nitro group; and aryl groups such as a phenyl group and a p-methoxyphenyl group.

Examples of the alkenyl groups represented by X include a vinyl group, a propenyl group, a methallyl group, a butenyl group, a prenyl group and an octenyl group. Examples of the alkoxyl groups represented by X include a methoxy group, an ethoxy group and an isopropoxyl group. These alkenyl groups and alkoxyl groups may be substituted with, e.g., halogen atoms such as a chlorine atom, a bromine atom, an iodine atom and a fluorine atom; alkoxyl groups such as a methoxy group, an ethoxy group, a propoxy group and a butoxy group; a hydroxyl group; tri-substituted silyloxy groups such as a tert-butyldimethylsilyloxy group and tert-butyldiphenylsilyloxy group; a nitro group; and aryl groups such as a phenyl group and a p-methoxyphenyl group.

Examples of the halogen atoms represented by each of X, $R^2$, $R^3$, $R^{31}$ and $R^4$ include a fluorine atom, a chlorine atom, a bromine atom and an iodine atom.

Examples of the alkyl groups represented by $R^6$ include linear or branched alkyl groups such as a methyl group, an ethyl group, a propyl group, an isopropyl group, a butyl group, an isobutyl group, a tert-butyl group and a hexyl group.

Examples of the alkali metal represented by M include lithium, sodium and potassium, and examples of the alkaline earth metal represented by M include magnesium and calcium.

Next, the present invention will be described in detail with each step:

Step (a)

The 2-sulfonylpyridine derivative (III) is obtained by reacting the sulfonyl cyanide (II) with the α, β-unsaturated carbonyl compound (I).

The reaction in this step (a) is usually performed in the presence of a solvent. There are no special restrictions to the solvent that is used as long as it will not have detrimental effects on the reaction. Examples of the solvents include aliphatic hydrocarbons such as pentane, hexane, heptane, octane and petroleum ether; aromatic hydrocarbons such as benzene, toluene, xylene and cumene; ethers such as diethyl ether, tetrahydrofuran, diisopropyl ether, dimethoxyethane and dibutyl ether; nitrites such as acetonitrile, propionitrile and benzonitrile; halogenated hydrocarbons such as methylene chloride, chloroform, carbon tetrachloride, dichloroethane and trichloroethane; dimethyl sulfoxide; and mixtures thereof. The amount of solvent used is preferably within a range of 0.1 to 200 times part by weight relative to the sulfonyl cyanide (II).

The reaction is performed in the presence or absence of a catalyst, and an acid catalyst or an ammonium salt, etc., is used as the catalyst. Examples of acid catalysts include boric acid and esters thereof such as triethyl borate and tributyl borate; phosphoric acid and esters thereof such as tributyl phosphate; alkali metal salts of perchloric acid such as sodium perchlorate and lithium perchlorate; weakly acidic ion-exchange resins such as IRC-50 (Organo Co., Ltd.). Moreover, Examples of ammonium salts include ammonium chloride and benzyltrimethylammonium chloride. The amount of catalyst used is preferably within a range of 0.01 to 1 equivalent per the sulfonyl cyanide (II).

Moreover, the reaction can be performed in the presence of an alcohol. Examples of the alcohols include methanol, ethanol, isopropanol, butanol and isoamyl alcohol. The amount of alcohol used is preferably within a range of 0.1 to 200 equivalents per the sulfonyl cyanide (II).

The reaction is preferably performed while refluxing the mixed solution of a solvent, the α, β-unsaturated carbonyl compound (I) and the sulfonyl cyanide (II). There are no special restrictions to the amount of the sulfonyl cyanide (II) used per the α, β-unsaturated carbonyl compound (I), but it is preferred that the sulfonyl cyanide (II) can be used within a range of 0.5 mole to 1 mole per 1 mole of the α, β-unsaturated carbonyl compound (I). Moreover, the reaction temperature is preferably within a range of from 0° C. to 200° C., more preferably within a range of from 80° C. to 120° C.

The 2-sulfonylpyridine derivative (III) obtained in this way can be isolated and purified by methods normally used to isolate and purify organic compounds. For example, the derivative (III) can be recrystallized and thereby purified by concentrating and cooling the reaction mixture. Moreover, it is possible to concentrate the reaction mixture as is and then purify the crude product that is obtained by distillation, chromatography, etc., as necessary.

In addition, water is generated as the reaction proceeds, but the 2-sulfonylpyridine derivative (III) can be obtained in a high yield by performing the reaction while removing the water. There are no special restrictions to the method for removing the water, but the water can be efficiently removed by using a solvent that is an azeotrope with water and performing azeotropic distillation to outside the system using the solvent. Moreover, a dehydrator that will not have a detrimental effect on the reaction, such as molecular sieves, etc., can also be present within the system.

Furthermore, the α, β-unsaturated carbonyl compound (I) and the sulfonyl cyanide (II) used as the starting materials are both known compounds and can be easily acquired or produced. For instance, the α, β-unsaturated carbonyl compound (I) can be synthesized by aldol condensation (refer to, for instance, Japanese Patent Application Laid-open No.9-59201 and U.S. Pat. No. 4,873,362). Moreover, the sulfonyl cyanide (II) can be produced by reacting a corresponding sulfinic acid metal salt with halogenated cyanogen (refer to *Organic Synthesis*, volume 6, page 727 (1988)).

Step (a')

The sulfonyl cyanide (II) is reacted with the halogeno-α, β-unsaturated carbonyl compound (I-1) to obtain the 4-halogeno-2-sulfonylpyridine derivative (III-1), which is the starting material for producing the 2-{[(2-pyridyl) methyl]thio}-1H-benzimidazole skeleton. The 4-chloro-3,5-dimethyl-2-sulfonylpyridine derivative (III-1a), where $R^1$ is a hydrogen atom, $R^2$ and $R^4$ are both methyl groups and $R^{31}$ is a chlorine atom, is particularly preferred as the derivative (III-1).

Furthermore, this step (a') can be executed by conducting the same procedure as in step (a), with the exception that $R^3$ of the α, β-unsaturated carbonyl compound (I) is limited to a halogen atom ($R^{31}$)

Step (b)

The 2-methylthio-1H-benzimidazole derivative (IV) is reacted with the 4-halogeno-2-sulfonylpyridine derivative (III-1) in the presence of an organolithium compound to obtain the 2-{[(4-halogeno-2-pyridyl)methyl]thio}-1H-benzimidazole derivative (V).

The 2-{[(4-chloro-3,5-dimethyl-2-pyridyl)methyl]thio}-1H-benzimidazole derivative (V-1) is particularly preferred as the derivative (V) where $R^1$ is a hydrogen atom, $R^2$ and $R^4$ are both methyl groups and $R^{31}$ is a chlorine atom.

Examples of the organolithium compounds that is used include alkyllithium compounds such as methyllithium, n-butyllithium, sec-butyllithium, and tert-butyllithium; aryllithium compounds such as phenyllithium; alkenyllithium compounds such as vinyllithium; and lithium amide compounds such as lithium diisopropylamide, and lithium bis-trimethylsilylamide. Of these, alkyllithium compounds are preferably used. There are no restrictions in a strict sense to the amount of organolithium compound that is used, but it is preferred that the organolithium compound can be used within a range of 1 mole to 10 moles per 1 mole of the 2-methylthio-1H-benzimidazole derivative (IV), and from the point of smooth progression of the reaction, it is further preferred that the organolithium compound can be used within a range of 2 moles to 3 moles per 1 mole of the 2-methylthio-1H-benzimidazole derivative (IV).

The amount of the 4-halogeno-2-sulfonylpyridine derivative (III-1) used is preferably within a range of 1 mole to 10 moles, more preferably within a range of 1 mole to 2 moles, per 1 mole of the 2-methylthio-1H-benzimidazole derivative (IV).

The reaction is preferably performed in the presence of a solvent. There are no particular restrictions to the solvent that is used as long as it will not have a detrimental effect on the reaction, and examples of the solvents include aliphatic hydrocarbons such as pentane, hexane, heptane, octane and petroleum ether; aromatic hydrocarbons such as benzene, toluene, xylene and cumene; and ethers such as diethyl ether, tetrahydrofuran, diisopropyl ether, dimethoxy ethane and dibutyl ether. One of these solvents can be used alone, or 2 or more can be mixed and used together. The amount of solvent used is preferably within a range of 0.5 to 50 times part by weight, more preferably within a range of 3 to 20 times part by weight relative to the 2-methylthio-1H-benzimidazole derivative (IV).

Moreover, a tertiary amine compound, such as triethylamine, tributylamine, trioctylamine, N,N,N',N'-tetramethylethylenediamine, 1,4-diazabicyclo[2.2.2]octane and 1,8-diazabicyclo[5.4.0]-7-undecene, etc., can be further added to the reaction system for the purpose of promoting the reaction under moderate conditions. Of these, 1,4-diazabicyclo[2.2.2]octane is preferred. There are no special restrictions to the amount used when a tertiary amine compound is added, but 1 mole or more per 1 mole of the organolithium compound is preferred, and within a range of 1 mole to 2 moles is further preferred, from the point of realizing the above mentioned purpose.

The reaction temperature can be selected as needed from within a range of from −100° C. to the boiling point of the solvent that is used, and a range of from −50° C. to 0° C. is further preferred.

This reaction is performed, for instance, as follows: That is, the 2-methylthio-1H-benzimidazole derivative (IV) and a solvent are mixed and brought to a specific temperature, a solution of the organolithium compound is added dropwise to the mixture, next, the 4-halogeno-2-sulfonylpyridine derivative (II-1) dissolved in the solvent is added dropwise at a specific temperature, and then the reaction mixture is agitated at the same temperature until the 2-methylthio-1H-benzimidazole derivative (IV) disappears. It is preferred that when the tertiary amine compound is added, it be added before dropwise addition of the solution of the organo-lithium compound.

The 2-{[(4-halogeno-2-pyridyl)methyl]thio}-1H-benzimidazole derivative (V) that is obtained in this way can be isolated and purified by methods normally used to isolate and purify organic compounds. For example, the derivative (V) can be isolated and purified by adding water to the reaction solution, the organic layer is separated, the aqueous layer is extracted with an organic solvent, the extract and the organic layer are combined, dried and then concentrated to give the desired product and when necessary, the product is further purified by recrystallization, chromatography, etc. Moreover, this product can be used as is in step (c) described below without being purified.

Furthermore, the 2-methylthio-1H-benzimidazole derivative (IV) can be easily synthesized by reacting a phenylenediamine derivative represented by general formula (IX)

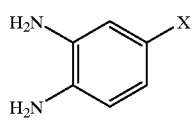

(IX)

(In the formula, X is the same as previously defined.) with carbon disulfide in the presence of zinc metal and an acid to obtain the 2-mercapto-1H-benzimidazole derivative (refer to, for instance, European Patent Application No. 609909A1), and then methylation of the 2-mercapto-1H-benzimidazole derivative.

Step (c)

The 2-{[(4-alkoxy-2-pyridyl)methyl]thio}-1H-benzimidazole derivative (VII) is obtained by reacting the 2-{[(4-halogeno-2-pyridyl)methyl]thio}-1H-benzimidazole derivative (V) and the metal alkoxide (VI).

Examples of the metal alkoxides (VI) include sodium methoxide, sodium ethoxide, potassium methoxide, lithium methoxide, sodium isopropoxide, potassium tert-butoxide, magnesium dimethoxide and calcium dimethoxide, and of these, sodium methoxide is particularly preferred. The amount of metal alkoxide (VI) used is preferably within a range of 0.1 mole to 10 moles, more preferably within a range of 1 mole to 2 moles per 1 mole of the 2-{[(4-halogeno-2-pyridyl)methyl]thio}-1H-benzimidazole derivative (V).

The reaction is preferably performed in the presence of a solvent. There are no particular restrictions to the solvent that is used as long as it will not have detrimental effects on the reaction. Examples of the solvents include alcohols such as methanol, ethanol, isopropyl alcohol and n-butanol; aliphatic hydrocarbons such as pentane, hexane, heptane, octane and petroleum ether; aromatic hydrocarbons such as benzene, toluene, xylene and cumene; ethers such as diethyl ether, tetrahydrofuran, diisopropyl ether, dimethoxy ethane and dibutyl ether; and aprotic solvents such as dimethylsulfoxide and N,N-dimethylformamide. One of these solvents can be used alone, or 2 or more can be used as a mixture. The amount of solvent is preferably within a range of 0.5 to 50 times, more preferably 3 to 10 times by weight relative to the 2-{[(4-halogeno-2-pyridyl)methyl]thio}-1H-benzimidazole derivative (V).

The reaction temperature can be selected as needed from within a range of from 20° C. to the boiling point of the solvent that is used, and a range of from 30° C. to 100° C. is further preferred.

This reaction is, for instance, performed as described below: That is, specific amounts of the 2-{[(4-halogeno-2-pyridyl)methyl]thio}-1H-benzimidazole derivative (V), the metal alkoxide (VI) and a solvent are mixed and agitated at a specific temperature until the 2-{[(4-halogeno-2-pyridyl) methyl]thio}-1H-benzimidazole derivative (V) disappears.

The 2-{[(4-alkoxy-2-pyridyl)methyl]thio}-1H-benzimidazole derivative (VII) thus obtained can be isolated and purified by methods normally used to isolate and purify organic compounds. For instance, water is added to the reaction solution and the organic layer is separated, the aqueous layer is extracted with organic solvent, the extract and the organic layer are combined, dried and then concentrated to give the desired, crude product, and when necessary, the crude product is further purified by recrystallization, chromatography, etc.

Step (d)

The 2-methylthio-1H-benzimidazole derivative (IV) is reacted with the 4-alkoxy-2-sulfonylpyridine derivative (VIII) in the presence of an organolithium compound to obtain the 2-{[(4-alkoxy-2-pyridyl)methyl]thio}-1H-benzimidazole derivative (VII).

This step (d) can be performed by conducting the same procedure as in step (b), with the exception that the 4-alkoxy-2-sulfonylpyridine derivative (VIII), which is a compound where $R^{31}$ of the 4-halogeno-2-sulfonylpyridine derivative (III-1) is substituted with alkoxyl groups (—$OR^6$), is used. Here, the 4-methoxy-3,5-dimethyl-2-sulfonylpyridine derivative (VIII-1) is particularly preferred as the derivative (VIII) where $R^1$ is a hydrogen atom and $R^2$, $R^4$ and $R^6$ are all methyl groups.

The 2-{[(4-alkoxy-2-pyridyl)methyl]thio}-1H-benzimidazole derivative (VII) obtained in this way can be easily converted to the 2-{[(4-alkoxy-2-pyridyl)methyl] sulfinyl)-1H-benzimidazole derivative, typically, omeprazole (2-{2-[(3,5-dimethyl-4-methoxypyridyl)methyl] sulfinyl}-(5-methoxy)-1H-benzimidazole), by an oxidation reaction.

EXAMPLES

The present invention will now be described in further detail using the following examples, but the present invention is not in any way limited to these examples.

Example 1

First, 8.05 g (113 mmol) of crotonaldehyde (2-butenal) and 9.17 g (54.9 mmol) of benzenesulfonyl cyanide were introduced to a 3-necked flask (50 ml volume) equipped with a thermometer, a magnetic stirrer, a Dean-Stark water type distilling receiver, and a condenser tube. Toluene (15 ml) as a solvent and butanol (1.5 ml) were added, and then 589 mg (5.55 mmol) of lithium perchlorate was added. Next, the mixture was heated under reflux for 15 hours while agitating at an internal temperature of 110° C. in a nitrogen atmosphere, and separating and removing water that was produced. After this solution was cooled to room temperature, the low-boiling components, such as solvent, etc., were removed under reduced pressure and the resulting concentrate was cooled in an ice bath to precipitate crystals. The crystals were filtered with a glass filter and washed with 10 ml of toluene that had been cooled to 5° C. or lower. Then the crystal were dried for 2 hours in vacuo to give 10.8 g of 2-benzenesulfonylpyridine having the following properties as colorless crystals (purity of 99%, yield of 89% based on benzenesulfonyl cyanide).

Melting point: 90° C.–91° C.

$^1$H-NMR spectrum (270 MHz, CDCl$_3$, TMS, ppm), δ:7.51–7.62(m, 4 H), 7.93(t, 1H, J=7.9 Hz), 8.04–8.11(m, 2 H), 8.21(d, 1H, J=7.9 Hz), 8.68(d, 1H, J=4.0 Hz)

Example 2

First, 8.20 g (115 mmol) of crotonaldehyde and 9.55 g (57.2 mmol) of benzenesulfonyl cyanide were introduced to the same reaction vessel as in Example 1. Toluene (15 ml) was added as the solvent, and 1.33 g (5.78 mmol) of tributyl borate was added. Then the mixture was heated under reflux for 3 hours while agitating at an internal temperature of 110° C. in a nitrogen atmosphere, separating and removing water that was produced. After this solution was cooled to room temperature, the low-boiling components, such as solvent, etc., were removed under reduced pressure and the resulting concentrate was cooled in an ice bath to precipitate crystals. The crystals were filtered with a glass filter and washed with 10 ml of toluene that had been cooled to 5° C. or lower. Then the crystals were dried for 2 hours in vacuo to give 10.9 g of 2-benzenesulfonylpyridine as colorless crystals (purity of 98%, yield of 85% based on benzenesulfonyl cyanide).

Example 3

First, 8.22 g (115 mmol) of crotonaldehyde and 9.22 g (55.2 mmol) of benzenesulfonyl cyanide were introduced to the same reaction vessel as in Example 1. Toluene (15 ml) as the solvemnt and butanol (1.5 ml) were added, and 677 mg (5.55 mmol) of sodium perchlorate was added. Then the mixture was heated under reflux for 18 hours while agitating at an internal temperature of 110° C. in a nitrogen atmosphere, separating and removing water that was produced. After this solution was cooled to room temperature, the low-boiling components, such as solvent, etc., were removed under reduced pressure and the resulting concentrate was cooled in an ice bath to precipitate crystals. The crystals were filtered with a glass filter and washed with 10 ml of toluene that had been cooled to 5° C. or lower. Then the crystals were dried for 2 hours in vacuo to give 11.2 g of 2-benzenesulfonylpyridine as colorless crystals (purity of 98%, yield of 91% based on benzenesulfonyl cyanide).

Example 4

First, 10.16 g (145 mmol) of crotonaldehyde and 10.09 g (60.4 mmol) of benzenesulfonyl cyanide were introduced to the same reaction vessel as in Example 1. Toluene (15 ml) were added as the solvent, and the mixture was heated under reflux for 15 hours while agitating at an internal temperature of 110° C. in a nitrogen atmosphere, separating and removing water that was produced. After this solution was cooled to room temperature, the low-boiling components, such as solvent, etc., were removed under reduced pressure and the resulting concentrate was cooled in an ice bath to precipitate crystals. The crystals were filtered with a glass filter and washed with 10 ml of toluene that had been cooled to 5° C. or lower. Then the crystals were dried in vacuo for 2 hours to give 9.11 g of 2-benzenesulfonyl-pyridine as colorless crystals (purity of 90%, yield of 62% based on benzenesulfonyl cyanide).

Example 5

First, 8.40 g (100 mmol) tiglic aldehyde (trans-2-methyl-2-butenal) and 8.35 g (50.0 mmol) of benzenesulfonyl cyanide were introduced to the same reaction vessel as in Example 1. Toluene (15 ml) as the solvent and butanol (1.5 ml) were added, and the mixture was heated under reflux for 3 hours while agitating at an internal temperature of 110° C. in a nitrogen atmosphere, separating and removing water that was produced. After this solution was cooled to room temperature, the low-boiling components, such as solvent, etc., were removed under reduced pressure and the resulting concentrate was cooled in an ice bath to precipitate crystals. The crystals were filtered with a glass filter and washed with 10 ml of toluene that had been cooled to 5° C. or lower. Then the crystals were dried for 2 hours in vacuo to give 10.5 g of 2-benzenesulfonyl-5-methylpyridine with the following properties as colorless crystals (purity of 99%, yield of 88% based on benzenesulfonyl cyanide).

Melting point: 117° C.–118° C.

$^1$H-NMR spectrum (270 MHz, CDCl$_3$, TMS, ppm), δ:2.40(s, 3H), 7.52–7.60(m, 3H), 7.70(dd, 1H, J=1.8 Hz, 8.6 Hz), 8.03–8.07(m, 2H), 8.09(d, 1H, J=8.6 Hz), 8.50(d, 1H, J=1.8 Hz)

Example 6

First, 8.20 g (115 mmol) of crotonaldehyde and 9.55 g (57.2 mmol) of benzenesulfonyl cyanide were introduced to the same reaction vessel as in Example 1. Toluene (15 ml) as the solvent and butanol (1.5 ml) were added, and 1.33 g (5.78 mmol) of tributyl borate was added. Then the mixture was heated under reflux for 3 hours while agitating at an internal temperature of 110° C. in a nitrogen atmosphere, separating and removing water that was produced. After this solution was cooled to room temperature, the low-boiling components, such as solvent, etc., were removed under reduced pressure and the resulting concentrate was cooled in an ice bath to precipitate crystals. The crystals were filtered with a glass filter and washed with 10 ml of toluene that had been cooled to 5° C. or lower. Then the crystals were dried for 2 hours in vacuo to give 11.3 g of 2-benzenesulfonylpyridine as colorless crystals (purity of 99%, yield of 89% based on benzenesulfonyl cyanide).

Example 7

First, 8.20 g (115 mmol) of crotonaldehyde and 9.55 g (57.2 mmol) of benzenesulfonyl cyanide were introduced to the same reaction vessel as in Example 1. Diisopropyl ether (15 ml) as the solvent and butanol (1.5 ml) were added, and 1.33 g (5.78 mmol) of tributyl borate was added. Then the mixture was heated under reflux for 20 hours while agitating at an internal temperature of 83° C. in a nitrogen atmosphere, separating and removing water that was produced. After this solution was cooled to room temperature, the low-boiling components, such as solvent, etc., were removed under reduced pressure, and the resulting concentrate was cooled in an ice bath to precipitate crystals. The crystals were filtered with a glass filter and washed with 10 ml of isopropyl ether that had been cooled to 5° C. or lower. Then the crystals were dried for 2 hours in vacuo to give 11.9 g of 2-benzenesulfonylpyridine as colorless crystals (purity of 99%, yield of 94% based on benzenesulfonyl cyanide).

Example 8

First, 8.40 g (100 mmol) of tiglic aldehyde and 8.35 g (50.0 mmol) of benzenesulfonyl cyanide were introduced to the same reaction vessel as in Example 1. Butanol (15 ml) was added as the solvent, and 1.15 g (5.00 mmol) of tributyl borate were added. Then the mixture was heated under reflux for 4 hours while agitating at an internal temperature of 118° C. in a nitrogen atmosphere, separating and removing water that was produced. After this solution was cooled to room temperature, the low-boiling components, such as solvent, etc., were removed under reduced pressure and the resulting concentrate was cooled in an ice bath to precipitate crystals. The crystals were filtered with a glass filter and washed with 10 ml of isopropyl ether that had been cooled to 5° C. or lower. Then the crystals were dried for 2 hours in vacuo to give 9.81 g of 2-benzenesulfonyl-5-methylpyridine as colorless crystals (purity of 99%, yield of 83% based on benzenesulfonyl cyanide).

Example 9

First, 8.07 g (113 mmol) of crotonaldehyde and 9.69 g (58.0 mmol) of benzenesulfonyl cyanide were introduced to the same reaction vessel as in Example 1. Toluene (15 ml) as the solvent and butanol (1.5 ml) were added, and 1.45 g (5.80 mmol) of tributyl phosphate was added. Then the mixture was heated under reflux for 4 hours while agitating at an internal temperature of 116° C. in a nitrogen atmosphere, separating and removing water that was produced. After this solution was cooled to room temperature, the low-boiling components, such as solvent, etc., were removed under reduced pressure and the resulting concentrate was cooled in an ice bath to precipitate crystals. The crystals were filtered with a glass filter and washed with 10 ml of toluene that had been cooled to 5° C. or lower. Then the crystals were dried for 2 hours in vacuo to give 11.3 g of 2-benzenesulfonylpyridine as colorless crystals (purity of 99%, yield of 88% based on benzenesulfonyl cyanide).

Example 10

First, 9.00 g (107 mmol) of tiglic aldehyde and 8.35 g (50.0 mmol) of benzenesulfonyl cyanide were introduced to the same reaction vessel as in Example 1. Toluene (15 ml) as the solvent and butanol (1.5 ml) were added, and 0.30 g (4.85 mmol) of boric acid was added. Then the mixture was heated under reflux for 4 hours while agitating at an internal temperature of 119° C. in a nitrogen atmosphere, separating and removing water that was produced. After this solution was cooled to room temperature, the low-boiling components, such as solvent, etc., were removed under reduced pressure and the resulting concentrate was cooled in an ice bath to precipitate crystals. The crystals were filtered with a glass filter and washed with 10 ml toluene that had been cooled to 5° C. or lower. Then the crystals were dried for 2 hours in vacuo to give 11.1 g of 2-benzenesulfonyl-5-methylpyridine as colorless crystals (purity of 99%, yield of 94% based on benzenesulfonyl cyanide).

Example 11

First, 4.29 g (51.1 mmol) of tiglic aldehyde and 8.35 g (50.0 mmol) of benzenesulfonyl cyanide were introduced to the same reaction vessel as in Example 1. Toluene (15 ml) as the solvent and butanol (1.5 ml) were added, and 1.15 g (5.00 mmol) of tributyl borate was added. Then the mixture was heated under reflux for 6 hours while agitating at an internal temperature of 119° C. in a nitrogen atmosphere, separating and removing water that was produced. After this solution was cooled to room temperature, the low-boiling components, such as solvent, etc., were removed under reduced pressure and the resulting concentrate was cooled in an ice bath to precipitate crystals. The crystals were filtered with a glass filter and washed with 10 ml of toluene that had been cooled to 5° C. or lower. Then the crystals were dried for 2 hours in vacuo to give 10.5 g of 2-benzenesulfonyl-5-methylpyridine as colorless crystals (purity of 99%, yield of 89% based on benzenesulfonyl cyanide).

Example 12

First, 9.00 g (107 mmol) of senecialdehyde (3-methyl-2-butenal) and 8.35 g (50.0 mmol) of benzenesulfonyl cyanide were introduced to the same reaction vessel as in Example 1. Toluene (15 ml) as the solvent and butanol (1.5 ml) were added, and 0.30 g (4.85 mmol) boric acid were added. Then the mixture was heated under reflux for 3 hours while agitating at an internal temperature of 119° C. in a nitrogen atmosphere, separating and removing water that was produced. After this solution was cooled to room temperature, the low-boiling components, such as solvent, etc., were removed under reduced pressure and the resulting concentrate was cooled in an ice bath to precipitate crystals. The crystals were filtered with a glass filter and washed with 10 ml of toluene that had been cooled to 5° C. or lower. Then the crystals were dried for 2 hours in vacuo to give 8.50 g of 2-benzenesulfonyl-4-methylpyridine with the following properties as colorless crystals (purity of 99%, yield of 72% based on benzenesulfonyl cyanide).

Melting point: 128° C.–129° C.

$^1$H-NMR spectrum (270 MHz, CDCl$_3$, TMS, ppm), δ:2.47(s, 3H), 7.25(dd, 1H, J=1.6 Hz, 4.8 Hz), 7.53–7.62(m, 3H), 8.04–8.08(m, 2H), 8.10(d, 1H, J=1.6 Hz), 8.52 (d, 1H, J=4.8 Hz)

Example 13

First, 9.00 g (107 mmol) of tiglic aldehyde and 8.35 g (50.0 mmol) of benzenesulfonyl cyanide were introduced to the same reaction vessel as in Example 1. Toluene (15 ml) as the solvent and butanol (1.5 ml) were added, and 0.57 g (2.48 mmoles) of tributyl borate were added. Then the mixture was heated under reflux for 7 hours while agitating at an internal temperature of 119° C. in a nitrogen atmosphere, separating and removing water that was produced. After this solution was cooled to room temperature, the low-boiling components, such as solvent, etc., were removed under reduced pressure and the resulting concentrate was cooled in an ice bath to precipitate crystals. The crystals were filtered with a glass filter and washed with 10 ml of toluene that had been cooled to 5° C. or lower. Then the crystals were dried for 2 hours in vacuo to give 8.50 g of 2-benzenesulfonyl-5-methylpyridine as colorless crystals (purity of 99%, yield of 72% based on benzenesulfonyl cyanide).

Example 14

First, 9.80 g (100 mmol) of mesityl oxide (4-methyl-3-penten-2-one) and 8.35 g (50.0 mmol) of benzenesulfonyl cyanide were introduced to the same reaction vessel as in Example 1. Toluene (15 ml) as the solvent and butanol (1.5 ml) were added, and 1.15 g (5.00 mmol) of tributyl borate was added. Then the mixture was heated under reflux for 10 hours while agitating at an internal temperature of 116° C. in a nitrogen atmosphere, separating and removing water that was produced. After this solution was cooled to room temperature, the low-boiling components, such as solvent, etc., were removed under reduced pressure and the resulting concentrate was cooled in an ice bath to precipitate crystals. The crystals were filtered with a glass filter and washed with 10 ml of toluene that had been cooled to 5° C. or lower. Then the crystals were dried for 2 hours in vacuo to give 6.14 g of 2-benzenesulfonyl-4,6-dimethylpyridine with the following properties as colorless crystals (purity of 99%, yield of 49% based on benzenesulfonyl cyanide).

Melting point: 106° C.–107° C.

$^1$H-NMR spectrum (270 MHz, CDCl$_3$, TMS, ppm), δ:2.41(s, 3H), 2.50(s, 3H), 7.09(s, 1H), 7.49–7.62(m, 3H), 7.83(s, 1H), 8.08(m, 2H)

Example 15

First, 11.2 g (107 mmol) of 2-chloro-2-butenal and 8.35 g (50.0 mmol) of benzenesulfonyl cyanide were introduced to the same reaction vessel as in Example 1. Toluene (15 ml) as the solvent and butanol (1.5 ml) were added, and 1.30 g (5.65 mmol) of tributyl borate was added. Then the mixture was heated under reflux for 7 hours while agitating at an internal temperature of 121° C. in a nitrogen atmosphere, separating and removing water that was produced. After this solution was cooled to room temperature, the low-boiling components, such as solvent, etc., were removed under reduced pressure and the resulting concentrate was cooled in an ice bath to precipitate crystals. The crystals were filtered with a glass filter and washed with 10 ml toluene that had been cooled to 5° C. or lower. Then the crystals were dried for 2 hours in vacuo to give 8.87 g of 2-benzenesulfonyl-5-chloropyridine with the following properties as colorless crystals (purity of 98%, yield of 69% based on benzenesulfonyl cyanide).

Melting point: 154° C.–155° C.

$^1$H-NMR spectrum (270 MHz, CDCl$_3$, TMS, ppm), δ:7.50–7.68(m, 4H), 7.89(dd, 1H, J=2.3 Hz, 8.0 Hz), 8.02–8.09(m, 1H), 8.16(d, 1H, J=8.0 Hz), 8.60(d, 1H, J=2.3 Hz)

Example 16

Phosphoryl chloride (100 ml, 164.5 g, 1.07 mol) was added to a 3-necked flask (500 ml volume) equipped with a thermometer, a mechanical stirrer and a dropping funnel, and cooled to 0° C. Then 120 ml of N,N-dimethylformamide were added dropwise over a period of 1 hour while agitating. The mixture was agitated for 2 hours while keeping the internal temperature at 0° C. and then 100 ml (85.3 g, 0.99 mol) of 3-pentanone was added dropwise over a period of 1 hour to the mixture. After dropwise addition was completed, the internal temperature of the mixture was raised to room temperature and the mixture was further agitated for 2 hours. Then the reaction mixture was added dropwise to 500 g of ice. An organic layer was separated from the mixture, and an aqueous layer was extracted twice with 200 ml of ethyl acetate. The extract and above mentioned organic layer were combined, dried over anhydrous magnesium sulfate, and the solvent was removed under reduce pressure to give 3-chloro-2-methyl-2-pentenal (131.2 g, yield of approximately 100%).

Next, 13.25 g (100 mmol) of 3-chloro-2-methyl-2-pentenal obtained above and 8.35 g (50.0 mmol) of benzenesulfonyl cyanide were introduced to the same reaction vessel as in Example 1. Toluene (15 ml) as the solvent and butanol (0.7 ml) were added, and 1.15 g (5.00 mmol) of tributyl borate was added. Then the mixture was heated under reflux for 4 hours while agitating at an internal temperature of 122° C. in a nitrogen atmosphere, separating and removing water that was produced. After this solution was cooled to room temperature, the low-boiling components, such as solvent, etc., were removed under reduced pressure and the resulting concentrate was cooled in an ice bath to precipitate crystals. The crystals were filtered with a glass filter and washed with 10 ml of toluene that had been cooled to 5° C. or lower. Then the crystals were dried for 2 hours in vacuo to give 13.09 g of 2-benzenesulfonyl-4-chloro-3,5-dimethylpyridine with the following properties as pale yellow crystals (purity of 99%, yield of 93% based on benzenesulfonyl cyanide).

Melting point: 91° C.–92° C.

$^1$H-NMR spectrum (270 MHz, CDCl$_3$, TMS, ppm), δ:2.38(s, 3H), 2.79(s, 3H), 7.53–7.68(m, 3H), 7.97–8.00(m, 2H), 8.20(s, 1H)

Example 17

First, 0.96 g (6.00 mmol) of 3-methyl-1-phenyl-2-buten-1-one and 0.84 g (5.00 mmol) of benzenesulfonyl cyanide were introduced to a 3-necked flask (25 ml volume) equipped with a thermometer, a magnetic stirrer, a Dean-Stark water type distilling receiver and a condenser tube. Toluene (5 ml) as the solvent and butanol (0.5 ml) were added, and 0.12 g (0.50 mmol) of tributyl borate was added. Then the mixture was heated under reflux for 8 hours while agitating at an internal temperature of 112° C. in a nitrogen atmosphere, separating and removing water that was produced. After this solution was cooled to room temperature, the low-boiling components, such as solvent, etc., were removed under reduced pressure to give the desired, crude product. The crude product was recrystallized with 5 ml of ethyl acetate to give 0.42 g of 2-benzenesulfonyl-4-methyl-6-phenylpyridine with the following properties as colorless crystals (purity of 99%, yield of 28% based on benzenesulfonyl cyanide).

Melting point: 170° C.–171° C.

$^1$H-NMR spectrum (270 MHz, CDCl$_3$, TMS, ppm), δ:2.54(s, 3H), 7.42–7.46(m, 3H), 7.51–7.61(m, 3H), 7.67(s, 1H), 7.90–7.95(m, 3H), 8.14(dd, 2H, J=1.7 Hz, 8.4 Hz)

Example 18

First, 0.93 g (6.36 mmol) of 3-phenyl-2-butenal and 0.99 g (5.91 mmol) of benzenesulfonyl cyanide were introduced to a 3-necked flask (25 ml volume) equipped with a thermometer, a magnetic stirrer, a Dean-Stark water type distilling receiver, and a condenser tube. Toluene (5 ml) as the solvent and butanol (0.5 ml) were added, and 0.14 g (0.59 mmol) of tributyl borate was added. Then the mixture was heated under reflux for 2 hours while agitating at an internal temperature of 112° C. in a nitrogen atmosphere, separating and removing water that was produced. After this solution was cooled to room temperature, the low-boiling components, such as solvent, etc., were removed under reduced pressure to give the desired, crude product. The crude product was purified by silica gel column chromatography (eluting solvent: ethyl acetate/hexane=¼) to give 1.20 g of 2-benzenesulfonyl-4-phenylpyridine with the following properties as colorless crystals (purity of 99%, yield of 71% based on benzenesulfonyl cyanide).

Melting point: 145° C.–146° C.

$^1$H-NMR spectrum (270 MHz, CDCl$_3$, TMS, ppm), δ:7.49–7.70(m, 9H), 8.11(m, 2H), 8.43(d, 1H, J=2.0 Hz), 8.69(d, 1H, J=5.0 Hz)

Example 19

First, 106 mg (purity of 84%, 0.72 mmol) of cyclohexylidene acetaldehyde, 120 mg (0.72 mmol) of benzenesulfonyl cyanide, 17 mg (0.072 mmol) of tributyl borate, 11 mg (0.14 mmol) of 1-butanol, and molecular sieves 4A (310 mg) as dehydrator were introduced to a flask (5 ml volume). Toluene (1.5 ml) was added as the solvent, and the mixture was heated for 14 hours at an internal temperature of 110° C. After this solution was cooled to room temperature, the molecular sieves was filtered off and the low-boiling components, such as solvent, etc., were removed under reduced pressure to give the desired, crude product. The crude product was purified by silica gel column chromatography (eluting solvent: ethyl acetate/hexane=⅓) to give 31 mg of 1-benzenesulfonyl-5,6,7,8-tetrahydroisoquinoline with the following properties as yellow crystals (yield of 16% based on benzenesulfonyl cyanide).

Melting point: 109° C.–112° C.

$^1$H-NMR spectrum (270 MHz, CDCl$_3$, TMS, ppm), δ:1.80–1.86(m, 4H), 2.80–2.84(m, 2H), 3.26–3.31(m, 2H), 7.10(d, 1H, J=4.7 Hz), 7.55–7.64(m, 3H), 7.97–8.01(m, 2H), 8.17(d, 1H, J=4.7 Hz)

Example 20

First, 5.0 g (39.6 mmol) of 4-acetoxy-2-methyl-2-butenal, 7.05 g (39.6 mmol) of benzenesulfonyl cyanide, 0.91 g (4.0 mmol) of tributyl borate and 1-butanol (0.59 g, 7.9 mmol) were introduced to a 3-necked flask (100 ml volume) equipped with a thermometer, a magnetic stirrer, a Dean-Stark water type distilling receiver and a condenser tube. Toluene (20 ml) was added as the solvent. Then the mixture was heated under reflux for 22 hours while agitating at an internal temperature of 108° C. in a nitrogen atmosphere, separating and removing water that was produced. After this solution was cooled to room temperature, the low-boiling components, such as solvent, etc., were removed under reduced pressure to give the desired, crude product. The crude product was purified by silica gel column chromatography (eluting solvent: ethyl acetate/hexane =⅓) to give 2.62 g of 3-acetoxy-2-benzenesulfonyl-5-methylpyridine with the following properties as a brown, oily substance (yield of 24% based on benzenesulfonyl cyanide).

$^1$H-NMR spectrum (270 MHz, CDCl$_3$, TMS, ppm), δ:2.40(s, 3H), 2.42(s, 3H), 7.36(d, 1H, J=1.0 Hz), 7.50–7.65 (m, 3H), 8.00–8.03(m, 2H), 8.33(d, 1H, J=1.0 Hz)

As is clear from the above-mentioned examples, by means of the present invention, 2-sulfonylpyridine derivatives can be industrially obtained efficiently in a good yield under moderate conditions.

Reference 1

First, 18.00 g (100 mmol) of 2-mercapto-5-methoxy-1H-benzimidazole, 16.83 g (300 mmol) of potassium hydroxide, 75 ml of ethanol, and 50 ml of water were added to a 3-necked flask (300 ml volume) equipped with a thermometer, a mechanical stirrer and a dropping funnel, and cooled to 5° C. Next, 15.00 g (105 mmol) of iodomethane was added dropwise to this solution over a period of 30 minutes while keeping internal temperature at 10° C. or lower. Then the solution was agitated for 2 hours at 10° C. or lower. The reaction solution was neutralized with an aqueous 2N hydrochloric acid solution, then the ethanol was removed under reduced pressure to precipitate a colorless solid. This solid was filtered and dried under reduced pressure to give 19.19 g of 2-methylthio-5-methoxy-1H-benzimidazole (yield of 98.9%).

Reference 2

First, 43.11 g (50.1 mmol) of 3-pentanone, 43.11 g (1.35 mol) of methanol, and 0.43 g (2.26 mmol) of p-toluenesulfonic acid monohydrate were added to a 3-necked flask (300 ml volume) equipped with a thermometer, a mechanical stirrer and a dropping funnel, and cooled to 5° C. Next, 63.03 g (525 mmol) of trimethyl orthoacetate was added dropwise to this solution over a period of 90 minutes while keeping internal temperature at 10° C. or lower. Then the temperature of the reaction mixture was raised to room temperature and the reaction mixture was agitated for 2 hours. The reaction solution was neutralized with 1.0 g (4.63 mmol) of 25% sodium methoxide/methanol solution, and then distilled under reduced pressure to give 59.34 g of 3,3-dimethoxypentane (boiling point: 55–57° C./50 torr, yield of approximately 100%).

Next, 150.58 g (2.06 mol) of N,N-dimethylformamide was introduced to a 3-necked flask (300 ml volume) equipped with a thermometer, a mechanical stirrer and a dropping funnel, and 77 ml (0.83 mol) of phosphoryl chloride was added dropwise while keeping temperature at 20° C., and successively, 50.00 g (0.38 mol) of 3,3-dimethoxy pentane obtained above was added dropwise while keeping temperature at 30° C. or lower. After dropwise addition was completed, the mixture was agitated for 30 minutes at 40° C., and cooled to room temperature, and then added dropwise to 1,500 ml aqueous 15% sodium bicarbonate solution while keeping internal temperature at 10° C. or lower and agitated for 1 hour at room temperature. This mixture was extracted 3 times with 500 ml of ethyl acetate. The extracts were combined, and dried over anhydrous magnesium sulfate, and the solvent was removed under reduced pressure to the desired, crude product. The crude product was further distilled under reduced pressure to give 29.32 g of (E,Z)-3-methoxy-2-methyl-2-pentenal (boiling point: 75–80° C./12 torr, yield of 61.2% based on 3,3-dimethoxypentane).

Next, 18.16 g (141.9 mmol) of (E, Z)-3-methoxy-2-methyl-2-pentenal thus obtained, 44.55 g (436.8 mmol) of acetic anhydride, 3.61 g (44.0 mmol) of sodium acetate, and 1.80 g (14.7 mmol) of N,N-dimethylaminopyridine were added to a 3-necked flask (300 ml volume) equipped with a thermometer, a mechanical stirrer, and a dropping funnel, and the mixture was agitated for 7 hours at 90° C. The reaction solution was added dropwise to 600 ml aqueous 9% sodium bicarbonate solution to neutralize and extract 3 times with 200 ml of ethyl acetate. The extracts were combined, dried over anhydrous magnesium sulfate, the solvent was removed under reduced pressure and the resulting concentrate was further distilled under reduced pressure to give 14.40 g of 1-acetoxy-3-methoxy-2-methyl-1,3-pentadiene (boiling point: 36° C./0.15 torr, yield of 59.7% based on (E, Z)-3-methoxy-2-methyl-2-pentenal).

Reference 3

First, 10.0 g (58.8 mmol) of 1-acetoxy-3-methoxy-2-methyl-1,3-pentadiene obtained in Reference 2, 9.82 g (100 mmol) of benzenesulfonyl cyanide, and 0.1 g of hydroquinone were added to a 3-necked flask (50 ml volume) equipped with a thermometer, a mechanical stirrer and a dropping funnel, and the mixture was agitated for 3 hours at 110° C. The reaction solution was cooled to room temperature, and the solvent was removed under reduced pressure and the resulting concentrate was purified by silica gel column chromatography (eluting solvent: ethyl acetate/hexane=⅓) to give 7.77 g of 2-benzenesulfonyl-4-methoxy-3,5-dimethylpyridine (yield of 47.8% based on benzenesulfonyl cyanide) with the following properties.

$^1$H-NMR spectrum (270 MHz, CDCl$_3$, TMS, ppm), δ:2.27(s, 3H), 2.62(s, 3H), 3.78(s, 3H), 7.55(dd, 2H, J=6.9

Hz, 7.4 Hz), 7.63(dd, 2H, J=6.9 Hz, 7.4 Hz), 7.99(d, 2H, J=7.4 Hz), 8.20(s, 1H)

Example 21

First, 0.970 g (5 mmol) of 5-methoxy-2-methylthio-1H-benzimidazole obtained in Reference 1, 1.12 g (10 mmol) of 1,4-diazabicyclo[2.2.2]octane, and 5 ml of tetrahydrofuran as the solvent were intorduced to a 3-necked flask (50 ml volume) equipped with a thermometer and a magnetic stirrer under a nitrogen atmosphere, and cooled to 0° C. Then 6.1 ml of a hexane solution of n-butyllithium (1.66 mole/1, 10.1 mmol) was added dropwise to the mixture while keeping internal temperature at 5° C. or lower. The mixture was agitated for 1 hour at 5° C. and then cooled to −40° C. A tetrahydrofuran (5 ml) solution of 1.41 g (5 mmol) of 2-benzenesulfonyl-4-chloro-3,5-dimethylpyridine obtained in Example 16 was added dropwise to the mixture while keeping internal temperature at −40° C. or lower. After dropwise addition was complete, the mixture was agitated for 1 hour at an internal temperature of −40° C. and 10 ml of water was added. An organic layer was separated from the mixture, and the aqueous layer was extracted twice with 10 ml of ethyl acetate. The extracts and the above mentioned organic layer were combined and dried over anhydrous magnesium sulfate. Then the solvent was removed under reduced pressure to give 1.39 g of 5-methoxy-2-{[(4-chloro-3,5-dimethyl-2-pyridyl)methyl]thio}-1H-benzimidazole (yield of 92%) with the following properties.

$^1$H-NMR spectrum (270 MHz, DMSO-$d_6$, TMS, ppm), δ:2.31(s, 3H), 2.44(s, 3H), 3.77(s, 3H), 4.71(s, 2H), 6.74(dd, 1H, J=2.5 Hz, 8.9 Hz), 6.96(bs, 1H), 7.33(d, 1H, J=8.9 Hz), 8.27(s, 1H), 12.40(bs, 1H)

Example 22

First, 277 mg (0.92 mmol) of 5-methoxy-2-{[(4-chloro-3,5-dimethyl-2-pyridyl)methyl]thio}-1H-benzimidazole obtained in Example 21 and 1.00 g (5.20 mmol) of methanol 28% solution of sodium methoxide were introduced to a 3-necked flask (30 ml volume) equipped with a thermometer, a magnetic stirrer and a condenser tube, and the mixture was agitated for 10 hours while being slowly refluxed. Then the mixture was neutralized with dilute hydrochloric acid. Ethyl acetate (10 ml) was added thereto and an organic layer was separated, and an aqueous layer was extracted twice with 10 ml of ethyl acetate. The extracts and the above mentioned organic layer were combined and dried over anhydrous magnesium sulfate. The solvent was removed under reduced pressure to give 232 mg of 5-methoxy-2-{[(4-methoxy-3,5-dimethyl-2-pyridyl)methyl]thio}-1H-benzimidazole (yield of 85%) with revealing the properties.

$^1$H-NMR spectrum (270 MHz, DMSO-$d_6$, TMS, ppm), δ:2.26(s, 3H), 2.42(s, 3H), 3.59(s, 3H), 3.77(s, 3H), 4.62(s, 2H), 6.70(dd, 1H, J=3.0 Hz, 8.9 Hz), 6.90(bs, 1H), 7.27(d, 1H, J=8.9 Hz), 8.07(s, 1H), 12.30(bs, 1H)

Example 23

First, 0.582 g (3.0 mmol) of 5-methoxy-2-methylthio-1H-benzimidazole obtained in Reference 1, 0.672 g (6.0 mmol) of 1,4-diazabicyclo[2.2.2]octane and 20 ml of tetrahydrofuran as the solvent were added in a nitrogen atomosphere to a 3-necked flask (50 ml volume) equipped with a thermometer and a magnetic stirrer, and cooled to −60° C. Then 6.2 ml of a cyclohexane solution of sec-butyllithium (1.01 mole/1, 6.3 mmol) was added dropwise to the mixture while keeping an internal temperature at −50° C. or lower. The mixture was agitated for 1 hour at −50° C. Then a tetrahydrofuran (THF) solution (5 ml) of 0.831 g (3.0 mmol) of 2-benzenesulfonyl-4-methoxy-3,5-dimethylpyridine obtained in Reference 3 was added dropwise while keeping an internal temperature at −50° C. or lower. After the mixture was agitated for 30 minutes at −50° C., 10 ml of water was added to the mixture. An organic layer was separated from the mixture and the aqueous layer was extracted 3 times with 20 ml of ethyl acetate. The extracts and above mentioned organic layer were combined and dried over anhydrous magnesium sulfate. The solvent was then removed under reduced pressure to give 0.924 g of 5-methoxy-2-{[(4-methoxy-3,5-dimethyl-2-pyridyl)methyl]thio}-1H-benzimidazole (yield of 94%).

As is clear from the above mentioned examples, by means of the present invention, it is possible to produce 2-{[(2-pyridyl)methyl]thio}-1H-benzimidazole derivatives that are useful as the synthesis intermediates for 2-{[(2-pyridyl)methyl]sulfinyl}-1H-benzimidazole derivatives efficiently in a short process.

The entire contents of the claims, specifications, and claims of the Japanese Patent Application Laid-open Nos. 10-12554, 10-323653, and 10-323654 are hereby incorporated by reference.

What is claimed is:

1. A method for producing a 2-sulfonylpyridine derivative represented by the formula (III)

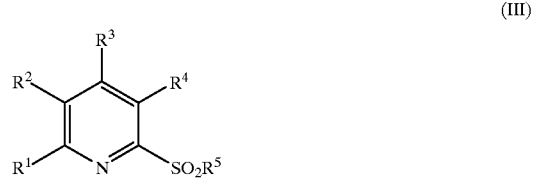

(III)

wherein $R^1$ is a hydrogen atom or an alkyl group or an aryl group that may be substituted, $R^2$ and $R^3$ are a hydrogen atom, a halogen atom, or an alkyl group or an aryl group that may be substituted, $R^4$ is a hydrogen atom, a halogen atom, an alkoxyl group, an alkylthio group, a cyano group, an acyloxy group, an alkoxycarbonyl group, a protected amino group that may be substituted, or an alkyl group or an aryl group that may be substituted, and together $R^2$ and $R^3$ or $R^3$ and $R^4$ can represent —$(CH_2)_n$— where n is 3 or 4, and $R^5$ is an alkyl group, a cycloalkyl group, an aryl group, or an aralkyl group that may be substituted, which method comprises:

reacting an α, β-unsaturated carbonyl compound represented by general formula (I)

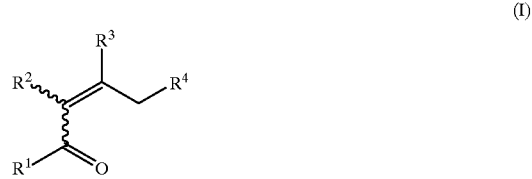

(I)

where $R^1$, $R^2$, $R^3$ and $R^4$ are the same as previously defined with a sulfonyl cyanide represented by general formula (II)

$$R^5SO_2CN \quad (II)$$

where $R^5$ is the same as previously defined to obtain the 2-sulfonylpyridine derivative represented by general formula (III).

2. A method for producing a 2-{[(4-alkoxy-2-pyridyl)methyl]thio}-1H-benzimidazole derivative (VII)

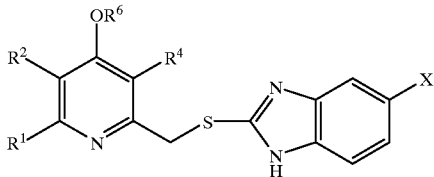
(VII)

where $R^1$ is a hydrogen atom or an alkyl group or an aryl group that may be substituted, $R^2$ is a hydrogen atom, a halogen atom, or an alkyl group or an aryl group that may be substituted, $R^4$ is a hydrogen atom, a halogen atom, an alkoxyl group, an alkylthio group, a cyano group, an acyloxy group, an alkoxycarbonyl group, a protected amino group that may be substituted, or an alkyl group or an aryl group that may be substituted, $R^6$ is an alkyl group, and X is a hydrogen atom, a halogen atom or an alkyl group, an alkenyl group, an aryl group, an aralkyl group or an alkoxyl group that may be substituted, which method comprises:

reacting a halogeno-α, β-unsaturated carbonyl compound represented by general formula (I-1)

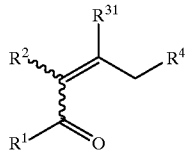
(I-1)

(In the formula, $R^1$, $R^2$ and $R^4$ are the same as previously defined, and $R^{31}$ is a halogen atom
with a sulfonyl cyanide represented by general formula (II)

 (II)

where $R^5$ is an alkyl group, a cycloalkyl group, an aryl group or an aralkyl group that may be substituted to obtain a 4-halogeno-2-sulfonylpyridine derivative represented by general formula (III-1)

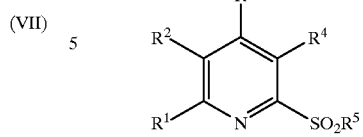
(III-1)

where $R^1$, $R^2$, $R^{31}$, $R^4$ and $R^5$ are the same as previously defined
reacting the obtained derivative of general formula (III-1) in the presence of an organolithium compound with a 2-methylthio-1H-benzimidazole derivative represented by general formula (IV)

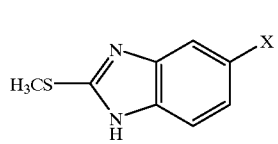
(IV)

where X is the same as previously defined
to obtain a 2-{[(4-halogeno-2-pyridyl)methyl]thio}-1H-benzimidazole derivative represented by general formula (V)

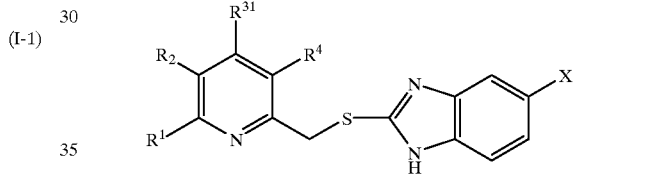
(V)

where $R^1$, $R^2$, $R^{31}$, $R^4$ and X are the same as previously defined,
reacting the obtained derivative of general formula (V) with a metal alkoxide represented by general formula (VI)

$R^6OM$ (VI)

were $R^6$ is the same as previously defined and M is an alkali metal or an alkaline earth metal,
to obtain the 2-{[(4-alkoxy-2-pyridyl)methyl]thio}-1H-benzimidazole derivative represented by general formula (VII).

* * * * *